United States Patent [19]
Shair et al.

[11] 3,964,294
[45] June 22, 1976

[54] TECHNIQUE AND SYSTEM FOR CODING AND IDENTIFYING MATERIALS

[75] Inventors: Frederick H. Shair, Altadena; Peter G. Simmonds, La Canada; Robert B. Leighton, Altadena; Peter J. Drivas, Pasadena, all of Calif.

[73] Assignee: California Institute of Technology, Pasadena, Calif.

[22] Filed: Nov. 1, 1974

[21] Appl. No.: 519,990

Related U.S. Application Data

[63] Continuation of Ser. No. 234,201, March 13, 1972, abandoned.

[52] U.S. Cl. ........................ 73/53; 44/59; 116/114 R; 252/408; 264/4
[51] Int. Cl.² ........................ G01N 31/08
[58] Field of Search .......... 73/53, 61.1 R; 356/36, 356/70; 40/326; 44/59; 252/408; 116/114 R; 264/4

[56] References Cited
UNITED STATES PATENTS

| | | | |
|---|---|---|---|
| 1,787,995 | 1/1931 | Reilly | 40/326 |
| 2,058,774 | 10/1936 | Colligan | 44/59 X |
| 2,088,412 | 7/1937 | Grosvenor | 40/326 |
| 2,278,413 | 4/1942 | Campbell | 40/326 X |
| 3,113,991 | 12/1963 | Kleber | 356/36 |
| 3,574,550 | 4/1971 | Scott et al. | 44/59 X |
| 3,691,983 | 9/1972 | Greenwood | 116/114 X |
| 3,733,178 | 5/1973 | Eriksen | 356/36 UX |
| 3,736,500 | 5/1973 | Berkowitz et al. | 44/59 X |
| 3,861,886 | 1/1975 | Meloy | 44/59 X |

OTHER PUBLICATIONS

Meloy, T.P., et al. *Coded Microspheres could Tag Oil.* In Chem. & Eng. News. vol. 49: p. 65. Apr. 12, 1971.

*Primary Examiner*—Richard C. Queisser
*Assistant Examiner*—Joseph W. Roskos
*Attorney, Agent, or Firm*—Lindenberg, Freilich, Wasserman, Rosen & Fernandez

[57] ABSTRACT

Microencapsulated spheroids containing a coded, volatile electron absorbing substance are dispersed into a material to be regulated such as crude oil in a tanker. Samples of the material such as an oil spill are collected and the source of the material is determined by electron capture gas chromatographic detection of the electron absorbing substance.

12 Claims, 3 Drawing Figures

TECHNIQUE AND SYSTEM FOR CODING AND IDENTIFYING MATERIALS

This application is a continuation of application Ser. No. 234,201, filed Mar. 13, 1972.

BACKGROUND OF THE INVENTION

1. Field of the Invention

The present invention relates to coded tagging of substances and more particularly, to a novel technique and system for identifying the source of oil spills and slicks.

2. Description of the Prior Art

There are several current serious situations which require improved means for identifying the vendors of certain materials. For example, certain ethical drugs are being overproduced and are finding their way into the illicit drug traffic. There is also a need to regulate and control the sale of explosives and ammunition. A most serious enforcement problem concerns the ability to identify the source of oil spills which are occuring at an ever increasing rate. Without the threat of prosecution of offenders by regulating agencies, the prospects of diminishing these activities are poor. The present analytical techniques are not sufficiently precise and exacting to stand the test of forensic attack.

According to the U.S. Coast Guard, in 1968 there were 714 major oil spills reported in U.S. waters. The problem of oil pollution is currently serious and is expected to grow more so with time. Oil pollution is illegal under at least six statutes of the U.S. code. One of the major problems in combatting oil pollution is to identify the polluter. Rapid and accurate identification of an oil spill out only aids in the forensic identification of the polluter, but can be of great value protecting those companies which have made significant efforts to improve their oil handling techniques. There are about 2,000 tankers making about 10,000 calls a year on U.S. Ports, with only 400 of these tankers flying the American flag. The international aspects compound the forensic problem, and the least that modern technology might contribute is in the providing of a rapid and accurate identification of the polluter.

Currently there are several techniques which have been proposed for the identification of oil spills which involve both passive tagging and active tagging.

Passive tagging is useful when the oils in a region of interest are so chemically diverse and so stable in the spill environment that a chemical fingerprint can be accurately determined in an analytical chemical laboratory. Techniques of passive tagging include (1) identification of heavy hydrocarbon fingerprint, (2) identification of trace metals such as vanadium and nickel and (3) identification of various sulfur-isotopic ratios. Less than half of the several hundred compounds appearing in any crude oil have yet to be identified. Due to rapid evaporation of the light fractions, photochemical oxidation, microbial oxidation, etc., passive tagging by means of the heavy hydrocarbons is quite limited in its usefulness. The usefulness of the trace metal passive tags is also severely limited because the associated inorganic compounds are generally soluble in water, and the associated organic compounds (vanadyl and nickel porphyrins) rapidly decompose when irradiated with ultraviolet radiation from the sun in the presence of oxygen.

Concerning the sulfur-isotopic ratio technique, unfortunately the isotopic ratios are known to be a general index of geological age and thereby not necessarily of location. Some of the isotopic ratios of Texas crude and Ontario crude, although separated by several thousand miles, are quite similar. Furthermore, the sulfur in oil is in a reduced state, but when spilled at sea begins to oxidize. Unfortunately, the compounds containing S-34 isotope, are more quickly oxidized than those containing the S-32 isotope, thus adding more uncertainty to the identification. Also microbial degradation results in fractionation of the lighter isotope.

Some authorities have recommended a combination of analytical techniques such as gas-liquid chromatography, controlled pyrolysis, mass spectrometry and computer calculations. In view of the above mentioned problems, it is believed that even a combination of these brute-force methods will be expensive and valueless.

The techniques of active tagging appear to be much more useful than those of passive tagging. Active tagging involves a coded material which is added to the oil. An ideal active tag would satisfy the following 10 criteria.

1. It must be an unusual material that is never found in the environment and is found only in the petroleum to which it has been added.
2. It must be compatible with (i.e., chemically unreactive and physically stable) and soluble or dispersible in the oil.
3. It must be both insoluble and nondispersible in water.
4. It must be relatively non-volatile.
5. It must be stable to chemical, photochemical, and microbial degradation in the oil-slick environment.
6. It must be easily detectable in extremely small quantities by readily available analytical techniques.
7. It must permit modifications so that when it is added to a particular oil shipment it provides a unique code or "license plate" for that carrier or transporter.
8. It must remain with the oil during the course of its history following a spill, and should then disappear from the surface.
9. It must in no way interfere with the end-use applications for that oil, nor complicate further processing and refining.
10. It must be available in quantity at economical prices.

Three techniques of active tagging are currently being tested. Techniques of active tagging include the use of (1) halogenated aromatic compounds identified with electron-capture gas chromatography, (2) organometallic compounds identified with standard spectroscopic methods, and (3) microspheroidal particles identified by size.

The organometallic tags include cyclohexanebutyrates and/or ethylhexanoates of Al, Ba, B, Cd, Ca, Cr, Co, Cu, Fe, Pb, Li, Mg, Mn, Hg, Ni, P, K, Si, Ag, NA, Sr, Sn, V and Zn. These compounds are stable, nonvolatile, oil soluble and are well characterized by a standard technique, emission spectroscopy. However, they can only be detected spectrographically in only about 1 part per million. Thus, one gram is needed per ton and at present the cost to tag a large tanker would be prohibitive.

There are other disadvantages to the use of these compounds. Only relatively few of the compounds are soluble in oil which limits the number of potential tags. Furthermore, most crude oils already contain many trace metals and microbial organisms are known to selectively accumulate certain trace metals.

The use of solid microspheroidal particle tags involves the use of well-characterized particles generally with diameters between 10–50 microns. There are several advantages of this tagging method. Only about $10^3$ particles/liter are needed. Thus with 10 micron particles only about 250 grams would be needed for a 500,000 ton tanker. Microspheroidal particles can be obtained in at least 11 distinct sizes between 10–50 microns in diameter and in at least 11 distinct density ranges between 0.9 and 1.5 grams/cm$^3$. A variety of materials can be made into microspheroids: metals, ceramics, nitrides, carbides, celluloses, starches, polystyrene, phenolic resins, and many organics. The particles can easily be separated from the oil-slick samples.

However, crude oil already contains particulate matter such as spores, pollens, microalgae, etc. which could interfere with or complicate the separation and characterization of the tag. Furthermore, the microsphere could undergo oxidation or microbial attack under the oil-spill environment.

The halogenated aromatics do not naturally occur in crude oil. Polynuclear hydrocarbons are more stable to oxidation than aliphatic compounds and halogenation decreases volatility. Many possible sites for substitution of the four halogens provide a large number of different compounds. The tag compounds are identifiable by electron capture G.C. in amounts as low as $10^{-12}$ grams.

However, relatively little is known about the stability of many of these compounds. The tag is chromatographed along with the oil slick giving rise to the possibility of interfering or overlapping with the tag's peak. It is possible that long after the peak has decomposed, that these relatively non-volatile compounds will persist, polluting the oceans surfaces and being entrained into new spills. Other compounds, such as polynuclear aromatic hydrocarbons, chlorinated biphenyls and pesticide residues all of which are present in the environment also give large signals in the electron capture detector.

OBJECTS AND SUMMARY OF THE INVENTION

It is therefore an object of this invention to provide a simple, reliable and inexpensive technique for coding chemical products.

Another object of the invention is to provide a novel active tagging technique for packaged industry suitable for use with electron-capture gas chromatography.

Yet another object of the invention is to identify oil spills by a novel active tagging technique which provides inexpensive and rapid identification of the source of the pollution.

A still further object of the invention is the provision of an active technique for tagging oil spills that is not affected by the oil environment, sea water environment nor does the tag deteriorate due to evaporation, photochemical oxidation, microbial oxidation or radiation with ultraviolet radiation from the sun in the presence of oxygen.

Containerized products, such as an oil tanker cargo is tagged and coded in accordance with the invention by dispersing coded, volatile electron absorbing substances microencapsulated in microspheroids throughout the oil tanker cargo to be regulated. A sample of the coded cargo such as an oil spill is collected and the source of the cargo and the identity of the polluter is determined by electron capture gas chromatographic detection of the coded, electron absorbing substances.

The encapsulation of the electron absorbing tag protects the tag from evaporation, oxidation, microbial attack, etc. By removing many restrictions heretofore deemed necessary for electron absorbing coded compounds such as the halogenated aromatic tagging system, only very small amounts, on the order of a pound of coded microcapsules would be needed to label a 500,000 ton tanker. The average cost of such a tag including microcapsulation would be below $15 per pound. The cost of the laboratory equipment is not high. The use of microencapsulated tags permits the use of more volatile compounds which significantly aids the analysis. There are many such compounds suitable for use such as halogenated, aliphatic compounds. With only 10 compounds, there can be $10^6$ different and distinct tags available for microcapsules containing up to six different compounds in varied and carefully controlled relative amounts. Further variation in distinction can be provided by the use of 10 separate particle sizes which would further permit up to $10^7$ different and distinct tags.

Since detection of the tag can be performed after it has been physically removed from the oil slick sample, no interference of the oil slick is possible. Thus, the final chromatogram will show those, and only those peaks associated with the tag. The forensic record would be conclusive and limited to the reliable information actually needed for the identification of the source, for example, six peaks, particle size and potentially the character of the encapsulating material. This type of data can be readily comprehended by laymen. At least three levels of redundancy can be built into the tagging system through the use of particle size, density, encapsulating coating and electron absorbing compounds.

Positive identification of the tag can be obtained and recorded in less than one hour after the sample has been collected. The detection technique is so sensitive that only one particle is actually needed to provide the identification. Though, even if 90% of the particles were lost in some manner, the volume of oil slick sample needed to provide identification would still be less than 10 cm$^3$. By using volatile compounds for the tag and an encapsulating material that would slowly decompose over an extended period, for example, a few years, build up on the ocean surface could be completely avoided.

The invention will now become better understood by reference to the following detailed description when considered in conjunction with the accompanying drawings.

DESCRIPTION OF THE PREFERRED EMBODIMENTS

Figure 1:
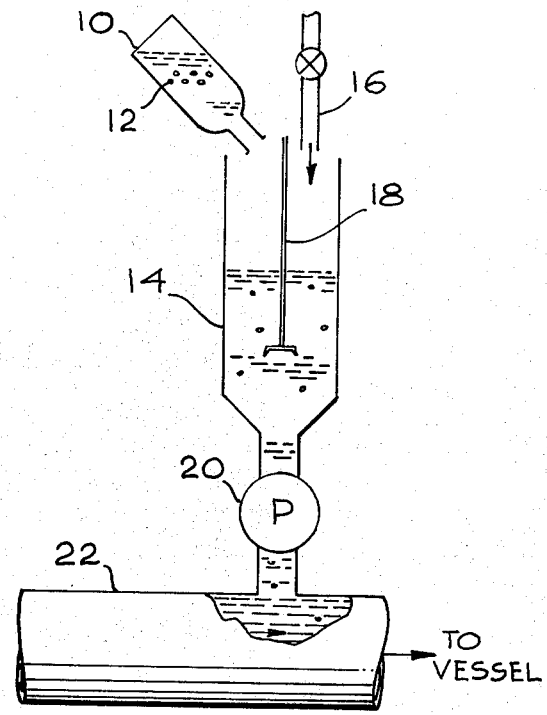
FIG. 1 is a schematic view of a system for coding an oil cargo.

The method of the invention is applicable to the encapsulation of many diverse types of active tags suitable for detection and identification by microanalytical techniques. However, the electron-capture (E.C.) detector is a substance-specific device. It is extremely sensitive to any molecular species which react with free electrons to form stable negative ions. The tag molecules are certain types containing electron absorbing atoms or groups, such as halogens, carbonyl, nitro groups, or certain condensed ring atomatics. The E.C. detector has very low sensitivity for hydrocarbons other than fused ring aromatics and very importantly the detector is extremely sensitive to halogen atoms. It can reliably detect halogenated hydrocarbons in quantities as low as $10^{-10}$ to $10^{-12}$ gram and under optimized conditions $10^{-14}$ grams have been detected.

Compounds which strongly capture the electrons have one or more of the following electrophore structures or substituents in their molecules: (1) —CO·CO—, (2) —CO·CH:CH·CO—, (3) the quinone structure (O), (4) —$NO_2$ and (5) —X where X is halogen. With substitution, the halogen affinities fall in the order I > Br > Cl > F. Multiple substitution by halogen or nitro groups more than linearly enhances the affinity for electrons. It appears that —CO in the electrophores listed above can be replaced by a phenyl group without great loss of affinity. Similarly, nitrogen can be substituted for carbon.

Table I lists the electron affinities relative to chlorobenzene as unity of some strong electron-attracting substances.

One iodine atom in a molecule caused about the same response in the same range as two bromine atoms or three chlorine atoms. Responses in molecules of different structures containing the same number of halogen atoms varied by one or two orders of magnitude. Responses varied by one to two orders of magnitude for the isomeric butyl chlorides, bromides, and iodides. While $SF_6$ and its telomers $SF_4(CF_2)_nCl$ gave high responses, the corresponding $SO_2X_2$ compounds have much lower sensitivities.

$SF_6$ and its telomers are a series of compounds very suitable for use as active tags in the system of this invention. The homologous telomers of the formula $SF_5(CF_2)_nZ$ where $n$ is an integer from 0–25 and Z is F, Br or I give very high responses. With only 10 of these compounds there can be $10^6$ distinctly distinguishable tagging permutations for microcapsules containing up to 6 compounds in controlled quantities. These compounds further satisfy the design criteria since they are not normally present in crude oil. Moreover, they exhibit a substantial vapor pressure at room temperature.

The correlation between chemical structure and column retention times or elution value is well recognized. It has been demonstrated experimentally that gas chromatography provides distinct separation and characterization of compounds such as halogenated aliphatic compounds. Furthermore, gas chromatographic treatment has the further advantages of separation and re-

TABLE I

| COMPOUNDS WITH HIGH ELECTRON AFFINITY | ELECTROPHORE | AFFINITY | COMPOUNDS WITH LOW ELECTRON AFFINITY | AFFINITY |
|---|---|---|---|---|
| Ethyl pyruvate | —CO.CO— | 1,700 | Ethyl acetate | <0.01 |
| Diacetyl | —CO.CO— | 2,000 | Acetylacetone | 1.2 |
| Dimethyl oxalacetate | —CO.CO— | 1,300 | Ethyl acetoacetate | 0.7 |
| Diethyl fumarate | —CO.CH:CH.CO— | 1,500 | Ethyl acrylate | 0.1 |
| Diethyl maleate | —CO.CH:CH.CO— | 1,700 | Diethyl malate | 0.01 |
|  |  |  | Diethyl succinate | <0.01 |
| Quinone | Q | 5,000 |  |  |
| Dimethylnaphthaquinone | Q | 4,100 | Hydroquinone | 0.1 |
| Benzaldehyde | —CO.P | 48 | Benzyl alcohol | 0.05 |
| Cinnamaldehyde | —CO.CH:CH.P | 310 |  |  |
| cis-Stilbene | P.CH:CH.P | 1 | Styrene | <0.01 |
| trans-Stilbene | P.CH:CH.P | 4 |  |  |
| Acetamide | —CO.NH. | 12 | Methyl amine | 0.01 |
| Azobenzene | P.N:N.P | 9 | Aniline | 0.1 |
| Diacetyldihydropyridine | Q | 4,000 | Pyridine | 0.02 |
| Anthracene |  | 12 | Phenanthrene | 0.05 |
| Azulene |  | 340 | Naphthalene | <0.01 |
| Cyclo-octatetrene |  | 210 | Cyclopentadiene | <0.01 |
| Carbon tetrachloride | —Cl | 7,000 | Ethane | <0.01 |
| Chloroform | —Cl | 800 |  |  |
| Hexachlorobenzene | —Cl | 1,100 | Benzene | <0.01 |
| Chlorobenzene | —Cl | 1 |  |  |
| Bromobenzene | —Br | 6 |  |  |
| Iodobenzene | —I | 370 |  |  |
| Nitrobenzene | —$NO_2$ | 390 |  |  |
| Dinitrophenol | —$NO_2$ | 1,450 |  |  |

P, phenyl radical.
Q, quinone structure.

In another survey of the response of an E.C. detector to halogenated substances it was found that low responses were shown by saturated and vinyl-type fluorinated hydrocarbons including those containing one chlorine atom. Compounds with the chlorine atom attached to a vinyl carbon gave lower responses than the corresponding saturated compounds. Attachment of the chlorine to an allyl carbon atom resulted in greater sensitivity than that obtained for the corresponding saturated compound. The response characteristics of the fluorinated cyclobutane closely resembled those of compounds with allyl $CF_3$ groups. The completely fluorinated benzene derivative $C_6F_6$ gave a high response.

moval of impurities that could interfere with the identification of the code.

In order to prepare the code, the retention time of each tag compound such as the homologous telomers are determined on a standardized gas chromatographic column and a standard reference list or catalog is prepared.

The first six labels in the code could contain just one of the telomers. Each label would then consist of 5 blanks and one indicative chromatogram peak. Each legal record would at most consist of 6 peaks and optionally a well characterized particle size analysis and analysis of the type of encapsulating material. The peaks can be quickly identified by comparison to the standard or catalog. The particular label is then established by a simple binary code for the presence or absence of each of the six telomer compounds.

The individual peaks should be clear and distinct since other analogous materials such as halogenated aromatics, halogenated heterocyclic compounds, and unhalogenated aliphatic compounds have different retention times and their detectability by the E.C. detector will not correspond to the behavior of the code compounds. If there should be overlapping or interfering peaks, the fraction can be rechromatographed under conditions providing a better resolution or on a different column.

An index of codes is prepared and each code is assigned an identification number. When the code is added to the cargo, the identity of the transporting vessel, shipper, ports of call and route are recorded. When an oil spill is sampled and analyzed, the index will be able to absolutely identify the source of pollution. It would be preferable to maintain the regulation of the index and addition of the code by government authority, whether of national or international jurisdiction to avoid duplication of codes and to assure that each and every cargo is appropriately labeled. It is also possible that some companies or an industry would adapt and implement the system on a voluntary basis to be able to avoid false accusation of pollution.

Apart from the type of material used for tagging, "codes" and "tagging profiles" will be involved in the system. Oil shipped into one port will be mixed upon unloading with oil from other tankers and hence the stored oil with its mixture of tagging codes will have its own unique tagging profile at a given time. Oil subsequently loaded onto a tanker will be re-tagged by the unique code assigned to the tanker. Thus, the re-tagged oil has a new tagging profile whose dominant code will be that of the tanker that last tagged the oil. As a result, any oil or oil slick from a tanker will have an underlying tag noise with a superimposed tanker code. To identify the source-last jurisdiction-of the oil not only must the individual tags be identified but also the relative abundance of each tag.

When an unknown batch of oil is recovered for source identification and analysis is begun, two immediate questions arise: Is this oil spilled from a tanker?- Who is the parent corporation? The first question arises because many ships as opposed to tankers, spill oil, and the second arises because oil is within a corporate jurisdiction much longer than in a tanker jurisdiction. To speed up analysis a special tag would be used to identify all oil ever transported by tanker. Since there are a few very large oil companies, special tags could be assigned to each of the large companies, and smaller companies and independents could be grouped and given a special tag for their group. This would be in addition to the unique tag or code of tags assigned to a tanker. Thus, a quick analysis could answer the question as to whether the oil was ever shipped by tanker and which is the overall company in charge of the oil. If an independent tanker carried the oil this would be readily seen.

The coded compounds are encapsulated in microcapsules by state of the art techniques. The microcapsules are preferably smooth, spheroids of well classified particle sizes so as to be able to further identify the particles by microscopic inspection or particle size analysis. Suitably the capsules are formed from an organic synthetic polymer having low solubility in the liquid tagged material and having low permeability to the volatile code material. A suitable encapsulating material for the halogenated aliphatic telomers in a urea-formaldehyde copolymer. If the permeability is suitably adjusted the volatile tag compounds can escape to the atmosphere over a period of several months and thus avoid buildup of the halogenated code compounds on the surface of the ocean. The wall thickness may vary over wide ranges but is suitably about 0.5 to $2\mu$ so as to be sufficient to encapsulate the code material yet allow crushing by ordinary force to release the volatile coding material for analysis.

It may be desirable to add another type of detectable compound to the encapsulating binder resin such as a fluorescent agent. This would again provide either a further element or redundancy or provide another indicia to the tag code extending the number of possible tags.

The micro-capsule particles should range in size from about 5–500 microns in diameter. It is preferable that the particles be spheroidal in nature for several reasons. The small surface area per unit volume and lack of areas of large surface curvature renders the particles relatively unsusceptible to chemical reactions. These properties also make it unlikely that the particles will clog or impact on passage through small apertures or adhere to interfaces. In fact, very small sizes, below 10 microns can be added to refined products such as fuel oil and will not effect the normal operation of burners or internal or external combustion engines. The very low concentration of particles also avoids interfering with subsequent processing of the oil.

Microspheroids are much more readily sized, for example by sieving sedimentation and microscopic methods, than any other shape. The flowability is important both in metering the particles into a large batch of material to be coded and in the preconcentration and isolation of a collected sample.

Particles can be well characterized by state of the art classifying techniques. Considering only particle sizes of 10–50 microns with an error of ± 2 microns for a given size there are at least 11 distinct and well-defined sizes. For densities over the range of 0.9 to 1.5 grams/ml and an error of ± 2 percent there are again at least 11 possible characterizations. It is preferred to adjust the density in the range of 1.0 to 1.2, suitably 1.1 grams/ml so that the microspheroids will tend to collect at the interface of the oil slick and water.

The encapsulated coded microspheres are readily dispersed into petroleum products. The metering of small amounts of liquids has been developed by the chemical pharmaceutical and processing industries. To aid in the injection of the tag, the coded microspheres as a homogenous phase should be diluted or dispersed in a non-solvent liquid carrier such as mineral oil to form a uniform suspension. The suspension is then uniformly injected into the petroleum so that the resulting tagged dispersion is also uniform.

There is ample evidence that stable dispersions of particles in a petroleum based liquid are easily produced. It is necessary to maintain this stability when the coded microsphere dispersion is injected into the petroleum. Surfactants are sometimes necessary to maintain stability. In crude oil, however, enough natural surfactants, such as porphyrins, are usually present to assure stability, especially for the dilute suspensions of interest in the present invention. Furthermore, the organic resin surface can be selected or modified to exhibit hydrophobic and oleophilic properties so that the necessary compatibility with the petroleum product is maintained.

Once a stable suspension of the coded microsphere particles is produced, it can be metered into petroleum without further problems. The suspension can be metered into petroleum as it passes through a pipeline or as it is pumped into a tanker. Many metering pumps are available at nominal cost. Some pumps through mechanical action on a diaphragm, bladder or flexible tube do not even contact the metered fluid suspension.

Referring now to FIG. 1, it is seen that the tagging sequence of the system of the invention first requires the assignment of a code to a particular batch, cargo or manufacturer and recording the assignment of the code. A bottle 10 containing the coded micropheres 12 is then emptied into a metering reservoir 14. A measured quantity of carrier liquid is added from inlet 16 and a uniform and stable suspension is formed by means of stirrer 18. The suspension is slowly metered by means of a pump 20 into the line 22 which is delivering crude oil to a vessel.

Figure 2:
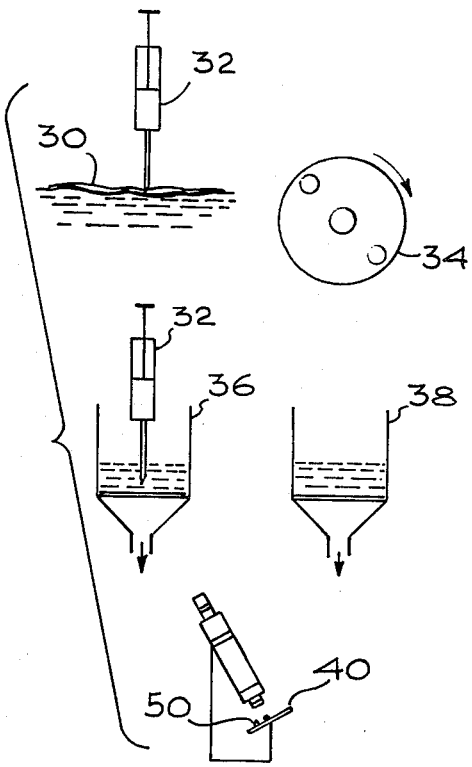
FIG. 2 is a schematic view of a technique for sampling an oil spill and isolating and characterizing the microspheres.

When it is desired to establish the source of a tagged material such as a pharmaceutical or petroleum product a representative sample is taken. Referring now to FIG. 2, in the case of an oil slick 30, a sample is removed from the slick by means of a syringe 32. The sample need not be larger than a few liters of liquid and can theoretically contain as few as one tracer particle. Even if 90% of the particles are lost from the oil slick, the volume of sample needed to provide identification would still be less than 100 cm$^3$.

Figure 3:
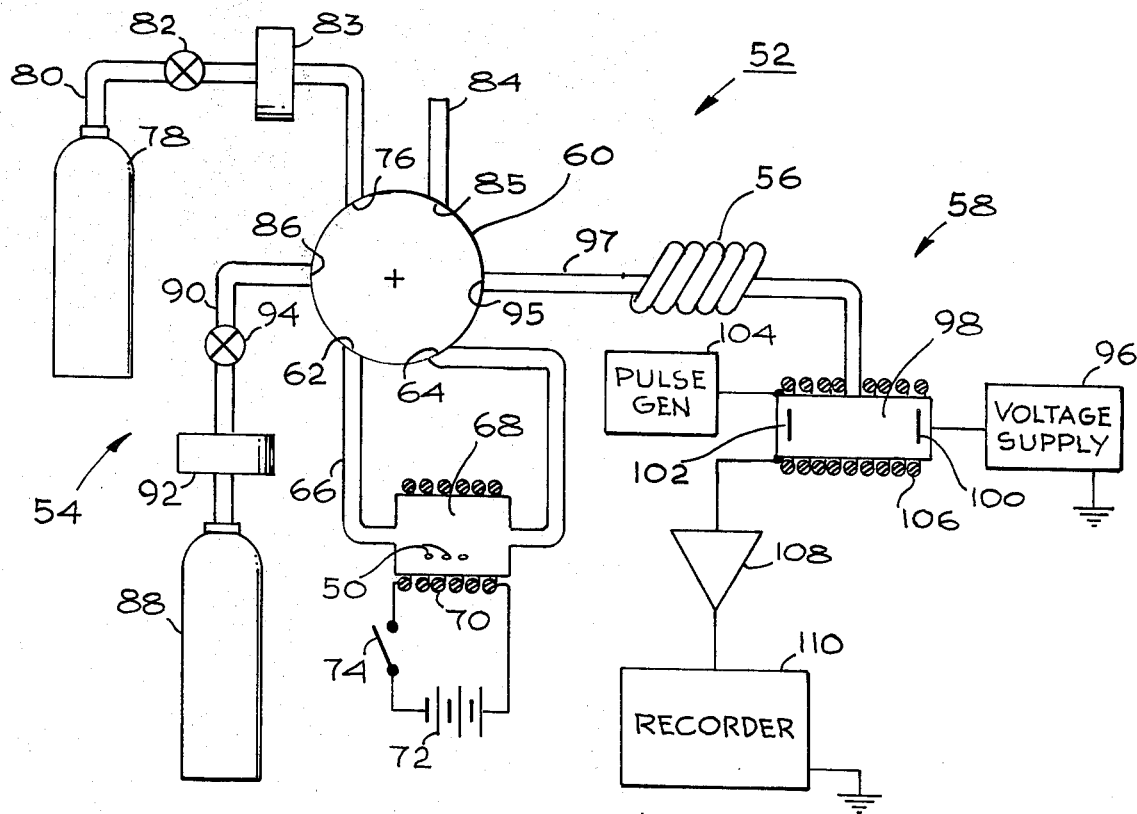
FIG. 3 is a schematic view of a G.C.-E.C. detector for use in the system of the invention.

The particles in the sample are preconcentrated by centrifugation in a centrifuge 34. The concentrated particles are placed on a first filter 36 and washed with a light hydrocarbon followed by a terminal filtration and wash on a Millipore filter 38. The particles are then placed on a microscopic mount 40 for particle size characterization and the density hardness, or actinic properties such as light absorption, fluorimetry or reflectance are determined before microanalysis. The washed and concentrated particles 50 are analyzed by an electron capture-gas chromatograph detector 52 as shown in FIG. 3.

The detector 52 includes a sampling section 54, a gas chromatographic column 56 and an electron capture detector 58. The sampling section includes a six port valve 60. Ports 62 and 64 are connected to the sample loop 66 which contains a sample chamber 68. The volume of the loop is calibrated to a known volume. The chamber 68 is surrounded by a heating coil 70 energized by power source 72 when switch 74 is closed.

Port 76 is connected to a regulated nitrogen supply 78 through a line 80 containing a valve 82 and a molecular sieve filter 83. Port 85 is connected to a vent 84. Port 86 is connected to a carrier gas supply 88, suitably an inert gas such as argon containing a small percentage of a thermallizing gas such as 5% methane or 0.3% hydrogen by means of a line 90. Line 90 also contains a molecular sieve filter 92 to remove water and other contaminants and a valve 94. A line 97 connects the G.C. column 56 to the port 95 and E.C. chamber 98.

The chamber of the E.C. detector 58 is suitably a plane parallel ionization chamber. A polarizing voltage supply 96 applies a potential across the detector 58. Electrons are set free in the chamber 98 by means of soft $\beta$-radiation from the cathode 100 which can be in the form of a sheet of metal coated with a thin layer of a tritium source. The density of free electrons in the chamber 98 is measured by periodically applying to the anode 102 a rectangular sampling pulse from a pulse generator 104. The duration of the pulse is chosen to be just sufficient to collect all electrons set free in the chamber, that is, capable of withdrawing a saturation current from the chamber. Such a pulse duration is, however, too short, to collect any of the relatively negative molecular ions.

The contribution to the total current flow of electrons liberated during the application of the pulse is only about 5 percent. The loss of electrons to the vapors of the electron absorbing tag compound is therefore observed effectively under free field conditions and when the energy of the electrons present is thermal. The chamber should be at constant temperature during measurement. The chamber may be surrounded by an electron heating coil 106 to heat the chamber to a constant temperature, suitably between 20°C to 100°C.

The quantity of electron absorbing compound should be adjusted such that the change in current in the electron capture chamber 98 does not exceed 10% of the total current. Above this value the change in current is no longer linearly related to vapor concentration. Quantities between $10^{-6}$ to $10^{-9}$ grams can be handled effectively with standard E.C. detectors. The current flow from the ionization chamber 98 is amplified by electrometer amplifier 108 and is recorded using a potentiometric recorder 110.

Before injection of sample into the G.C. column, the microcapsules 50 are placed in the sampling chamber 68 and switch 74 is closed to energize the coil 70. The heated microcapsules 50 burst and release vapors of electron absorbing compounds. The six port valve is positioned such that port 76 is connected to port 62 and port 64 is connected to port 85. When valve 82 is opened a regulated flow of purified nitrogen sweeps through the sample loop 66 and out the vent 84. At the same time port 86 is connected to port 95 and valve 94 is opened to establish a flow of carrier gas through the column 56 and to zero the detector 58.

During injection port 76 is connected to vent 84 through port 85 and port 86 is connected to port 62 and port 64 is connected to port 95. A measured plug of electron absorbing tag compound is delivered to the column 56 and the characteristic peaks are determined in the E.C. detector 58 and all recorded on recorder 110. The amount of each characteristic electron absorbing component of the sample can be determined from calibration runs of the identified compounds in the sample.

It is thus apparent that a simple, fool-proof and inexpensive and conclusive technique for oil spill identification is provided by the present invention. The tagging system of the invention totally avoids the problems of weathering associated with present active and passive tagging techniques.

It is also noted that although the specific embodiment is directed toward oil-slick identification, the technique of the invention has broad application to the tagging of solid, semi-solid or liquid systems for example in preparation of foods, such as cake mixes using edible carbohydrate capsules, in the blending of powders or liquids, and in tagging of cosmetic or pharmaceutical products, especially as a tracer of illicit or stolen drugs.

It is therefore to be understood that only preferred embodiments of the invention have been described and that numerous substitutions, modifications and alterations are all permissible without departing from the spirit and scope of the invention as defined in the following claims.

What is claimed is:

1. A method of tagging a material for future identification, said material being selected from the group consisting of petroleum crude oil and refined liquid products thereof, comprising the steps of adding to said material microcapsules encapsulating a detectable amount of a readily analyzable coded substance not normally present as a component of said material, dispersing said microcapsules uniformly throughout said material, said microcapsules having low solubility in said material and low permeability to said substance, collecting a sample of said material containing said microcapsules dispersed therein, concentrating said microcapsules, releasing said tag substance from said microcapsules and analyzing said substance by electron-capture gas chromatography.

2. A method according to claim 1 in which the material is an oil spill on surface water, the sample is removed from the spill the microcapsules are concentrated by centrifugation and filtering and the substance is released from the microcapsules by heating the microcapsules in the presence of a flowing stream of inert carrier gas.

3. A method according to claim 1 further including the steps of comparing the response of the electron-capture detector to a set of calibration peaks, identifying each peak and component of the substance and comparing the peaks to a reference to identify the tag and the source of the oil spill.

4. A composition of matter comprising a material to be identified in the future containing a dispersion of microcapsules encapsulating a coded, active tag substance consisting essentially of a compound not normally present as a component of the material and being readily detectable and analyzable when released from said microcapsule, wherein said material is selected from crude petroleum oil and refined liquid products thereof, said material contains no more than $10^{-8}$ parts of said substance and said substance is a mixture of electron absorbing compounds each containing at least one electrophore selected from —CO·CO—, —CO·CH:CH—CO—, quinone, —NO$_2$ and halogen, each of said compounds having a specific response to electron capture-gas chromatographic detection, and wherein said microcapsules have a wall thickness between 0.5 and 2 microns and a well characterized particle size between 5–50 microns, and said microcapsules have a density between 0.9 and 1.5 grams per cubic centimeter.

5. A method according to claim 4 in which the mixture is formed of telomers of the formula:

$$SF_5(CF_2)_n Z$$

where $n$ is an integer from 0–25 and Z is selected from F, Br or I.

6. A composition of matter comprising a material to be identified in the future containing a dispersion of microcapsules encapsulating a coded, active tag substance consisting essentially of a compound not normally present as a component of the material and being readily detectable and analyzable when released from said microcapsule, wherein said material is selected from crude petroleum oil and refined liquid products thereof, said material contains no more than $10^{-8}$ parts of said substance and said substance is a mixture of electron absorbing compounds each containing at least one electrophore selected from —CO·CO—, —CO·CH:CH—CO—, quinone, —NO$_2$ and halogen, each of said compounds having a specific response to electron capture-gas chromatographic detection, and wherein said microcapsules have a particle size between 5–500 microns and a density between 0.9 and 1.5 grams per cubic centimeter.

7. A composition according to claim 6 in which the mixture is formed of telomers of the formula:

$$SF_5(CF_2)_n Z$$

where $n$ is an integer from 0–25 and Z is selected from F, Br or I.

8. A method of tagging a plurality of separate quantities of a material for future identification comprising the steps of
   preparing a plurality of separate quantities of encoded, detectable amounts of readily analyzable, volatile, electron absorbing, tag materials, each said tag material differing from every other tag material by the presence or absence of a selected number of substances having specific responses to electron capture-gas chromatographic detection,
   encapsulating each separate quantity of tag material in separate pluralities of microspheres,
   adding each separate plurality of microspheres to each separate quantity of material to be tagged, and dispersing said microspheres substantially uniformly throughout each said separate quantity of material.

9. A method as recited in claim 8 wherein each separate quantity of said tag materials contains an electrophore group selected from the group consisting of —CO·CO—, —CO·CH:CH·CO—, quinone, —NO$_2$, and halogen.

10. A composition of matter comprising a material to be identified in the future containing a dispersion of microcapsules encapsulating a coded, active tag substance, said material having no more than $10^{-8}$ parts of said substance, said substance comprising a mixture of electron absorbing compounds each containing at least one electrophore selected from —CO·CO—, —CO·CH:CH—CO—, quinone, —NO$_2$, and halogen, each of said compounds having a specific response to electron capture-gas chromatographic detection.

11. A composition according to claim 10 in which the tag substance is formed of telomers of the formula:

$$SF_5(CF_2)_n Z$$

where $n$ is an integer from 0–25 and Z is selected from F, Br or I.

12. A composition of matter comprising a material to be identified in the future containing a dispersion of microcapsules encapsulating a coded, active tag substance which is formed of telomers of the formula:

$$SF_5(CF_2)_n Z$$

where $n$ is an integer from 0–25 and Z is selected from F, Br or I.

* * * * *